United States Patent [19]

Kasday

[11] Patent Number: 5,779,292
[45] Date of Patent: Jul. 14, 1998

[54] MANIPULATION AID FOR ATTACHMENT TO HUMAN BODY PARTS

[75] Inventor: Leonard Ralph Kasday, Moorestown, N.J.

[73] Assignee: Lucent Technologies Inc., Murray Hill, N.J.

[21] Appl. No.: 778,437

[22] Filed: Jan. 2, 1997

Related U.S. Application Data

[63] Continuation of Ser. No. 366,655, Dec. 30, 1994, abandoned.

[51] Int. Cl.$^6$ ................................. A61F 2/78; B25J 1/00
[52] U.S. Cl. ................................. 294/25; 224/218; 623/65
[58] Field of Search ................................. 294/1.1, 1.2, 15, 294/25, 26, 19.1; 30/298, 323, 327; 224/217–219, 222, 267; 379/456; 401/6–8; 414/9; 623/57, 65

[56] References Cited

U.S. PATENT DOCUMENTS

| | | | |
|---|---|---|---|
| 426,324 | 4/1890 | Ramsey | 401/8 X |
| 460,104 | 9/1891 | Barrett | 294/25 |
| 1,217,905 | 3/1917 | Boice | 294/25 X |
| 1,316,436 | 9/1919 | Feeney | 294/25 |
| 1,797,103 | 3/1931 | Rustad | 401/8 |
| 2,278,610 | 4/1942 | Brownson et al. | 294/25 |
| 2,866,440 | 12/1958 | Green | 401/8 X |
| 2,889,160 | 6/1959 | Nelson | 294/25 X |
| 3,729,035 | 4/1973 | Manzanarez | 294/25 X |
| 3,834,021 | 9/1974 | White et al. | 294/25 X |
| 3,942,194 | 3/1976 | Winter | 623/65 |
| 4,165,896 | 8/1979 | Hunt | 294/25 |
| 4,606,484 | 8/1986 | Winter et al. | |
| 4,951,856 | 8/1990 | Horgan | 224/218 |

FOREIGN PATENT DOCUMENTS

3540257  11/1986  Germany ........................ 414/9

OTHER PUBLICATIONS

Direct Safety Company, Ergonomics Catalog '94. pp. 17–22, 37–42.
UARCO Quality Business Products & Continuous Forms, pp. 72, 73.
Smith & Nephew Rolyan, 1994 Activities of Daily Living Products, p. 14A.
Direct Safety Company '94 Ergonomics Catalog, pp. 18–25.

*Primary Examiner*—Johnny D. Cherry

[57] ABSTRACT

The present invention relates to the field of manipulation aids, in particular, to a manipulation aid or pointing stick that attaches to a user's hand for pressing keys on a keyboard, turning pages or the like. In one embodiment of the inventions, a strap is adapted to engage the hand of a user. A cone, having a base and an apex, is mounted at its base to the strap. An actuator is mounted to the apex of the cone. The actuator includes a tip which can be seen by the user and can be used to press keys of a keyboard, turn pages of a book, etc. The manipulation aid is designed to collapse under a predetermined load to prevent unacceptably high forces from being delivered to the user's hand.

35 Claims, 2 Drawing Sheets

MANIPULATION AID FOR ATTACHMENT TO HUMAN BODY PARTS

This application is a continuation of application Ser. No. 08/366,655 filed on Dec. 30, 1994, now abandoned.

FIELD OF THE INVENTION

The invention relates to manipulation aids and, more particularly, to a pointing stick that attaches to a user's hand for pressing keys on a keyboard, turning pages, or the like.

BACKGROUND OF THE INVENTION

Some people do not have complete muscular or neurological control of their fingers, either temporarily or permanently. These people may have difficulty performing tasks typically done with fingers, such as using a keyboard, dialing a phone or turning pages of a book.

Pointing sticks have been developed to enable those with such physical challenges to use a keyboard. A cylindrical holder is positioned in the user's palm. The pointing stick is generally mounted to the holder and disposed perpendicularly to the axis of the holder such that the stick extends down, parallel to the user's palm. The user moves his hand over the key to be pressed, pushing the tip of the stick onto the proper key. A rubber tip can be attached to the stick to facilitate page turning.

Such a pointing stick is awkward to use, however, because it is difficult to see where the tip of the stick is located. Both the user's hand and the holder may block the user's view of the stick. Further, because the user is pressing the keys using his arm or hand, more force can be exerted than by simply using a finger. Consequently, there is a danger that the user's hand will be injured or the keyboard will be damaged by a hard stroke. Since the stick is disposed parallel to the user's palm, the user will generally hold his hand in a vertical position, which may not be the most natural position, resulting in discomfort.

SUMMARY OF THE INVENTION

The current invention comprises a manipulation aid that attaches to a body part of a user. A projection is attached to a strap. The strap is adapted to engage the body part of the user. An actuator is mounted to the projection such that it is clearly visible to the user when using the manipulation aid. The projection may be collapsible under a predetermined load to prevent the user from exerting too much force with the manipulation aid. The actuator may include a tip which can be seen by the user and can be used to press keys of a keyboard or to turn pages of a book, etc. A manipulation aid may be mounted to each hand to increase typing ability.

A more complete understanding of the present invention may be had by reference to the following description with the accompanying drawings.

DETAILED DESCRIPTION OF THE DRAWINGS

Figure 1:
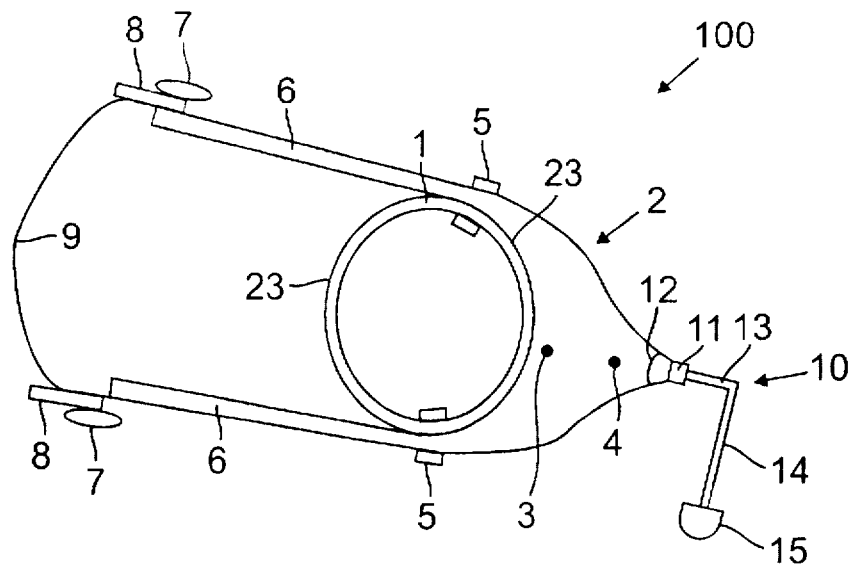
FIG. 1 is a side view of the manipulation aid of the present invention.

FIG. 1 is a side view of the manipulation aid 100 of the present invention. The aid 100 includes a projection or pointing stick, such as cone 2, which comprises a base 3 and an apex 4. The cone may be made of vinyl, rubber or other flexible material. Preferably, such a cone would be vinyl shaped into a hollow cone to reduce the weight of the manipulation aid 100 and to increase the flexibility of the cone. Alternatively, the cone can comprise a flexible foam cone covered with a cloth casing in which the casing compresses the foam slightly to increase its stiffness. Other mechanisms that collapse under a given load, such as a jointed stick with a spring lock, would also be acceptable projections. Of course, the vinyl must be thick enough to maintain its shape under load until a predetermined load is reached. The thickness will need to be determined depending on the intended use. As currently intended for use in depressing keyboard keys, the vinyl that is about 1/16 of an inch thick has been acceptable.

A tube 1, having an exterior wall 23, is mounted to the cone 2 near the base 3 by tacks 5. Other means of mounting the tube to the cone, such as by gluing or welding, would also be acceptable. Preferably, the tube is made of vinyl or other flexible materials. Preferably, both the cone and the tube are made of a flexible material. As discussed below, this permits the manipulation aid 100 to collapse when too much force is exerted on or by the user's hand. Of course, the cone could be made a rigid material such that only the tube collapses. Alternatively, the tube could be made of a rigid material so that only the cone collapses.

A harness or other means for engaging the tube 1 and the cone 2 to a user's body part is provided. For example, the tube and the cone could be mounted to the palm of a glove. As presently preferred, straps 6 are attached to the cone 2, extending away from the cone. In the embodiment of FIG. 1, the straps 6 are integrally formed with the base 3 of the cone 2. Consequently, the tacks 5 mount both the straps and the cone to the tube 1. Other means for attaching the straps to the cone would also be acceptable.

Buttons 7 are mounted to the straps 6 distal to the tube 1. A buckle 8 is mounted to each button. A belt 9 is slidably engaged to each buckle such that the length of the belt between the buckles can be adjusted. This permits the ends of the straps to be brought closer together or separated further apart to better fit the hand of the user. Other means for connecting the straps, such as snaps or hook and loop fasteners, would also be acceptable.

An actuator 10 is mounted to the cone 2 at the apex 4. A neck 11 of the actuator is disposed in a hole at the apex of the cone. The neck may be knurled or roughened to prevent it from rotating within the hole. A wire 12 is wrapped around the cone to prevent the neck from slipping out of the hole. The actuator could be attached to the cone in other manners and still practice the invention. The actuator could also be integrally formed with the cone, if desired. In any case, the cone provides a platform for the actuator, displacing the actuator from the palm of the hand.

The actuator 10 includes a rod 13 mounted to the neck 11. An arm 14 is mounted to the rod. A tip 15 is mounted on the arm distal to the rod. Preferably, the rod has a smaller cross-sectional area than the neck; this improves visibility of the tip for the user. As shown in FIG. 1, the arm is disposed at 90° with respect to the rod. However, other orientations may be used as well and still practice the invention. In particular, as discussed more fully below, the angular relationship of the arm to the rod should be selected based on user comfort.

Figure 2:
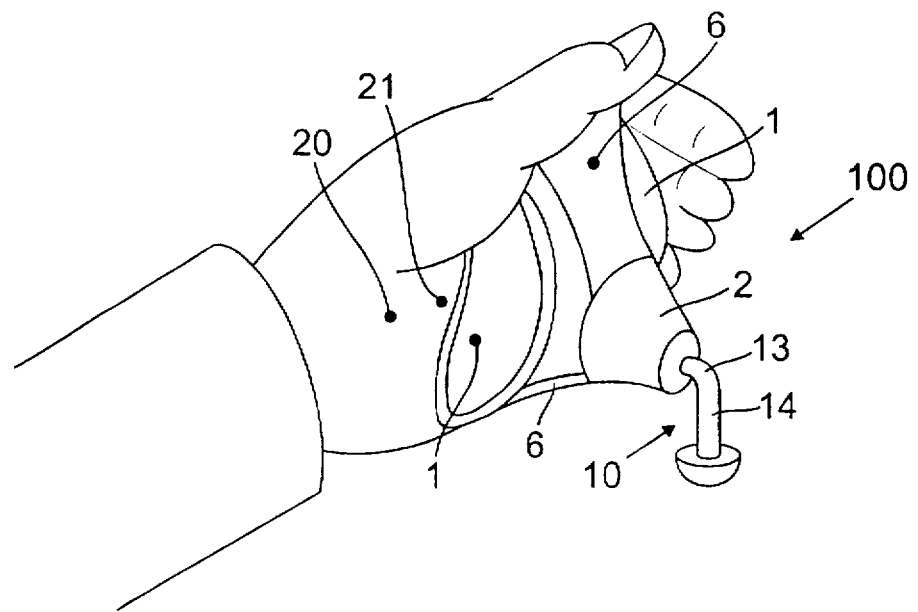
FIG. 2 is a perspective view of the manipulation aid of FIG. 1 shown mounted to the hand of a user.

FIG. 2 is a perspective view of the manipulation aid 100 of the present invention shown attached to a user's hand 20. A manipulation aid may be attached to each hand. The manipulation aid could also be attached to other parts of the user's body, such as the wrist or arm. The tube 1 is disposed in the palm 21 of the user's hand, keeping the cone a distance from the palm. Preferably, the tube is sized to fit comfortably in the palm. A radius of about 1⅝ inches and a height of 1.5 inches for the tube have been found acceptable. Other sizes could be used for different-sized hands. The cone 2 is disposed on the tube in front of the palm. The straps 6 extend around the tube 1 and around the back of the hand 20, thereby holding the manipulation aid in place. The actuator 10 is mounted to the cone such that the rod 13 extends substantially perpendicularly from the palm 21. As shown in FIG. 2, the arm 14 extends from the rod at an angle greater than 90° and points downwardly. The arm also may be disposed at other angles with respect to the rod, including 90°.

Figure 3:
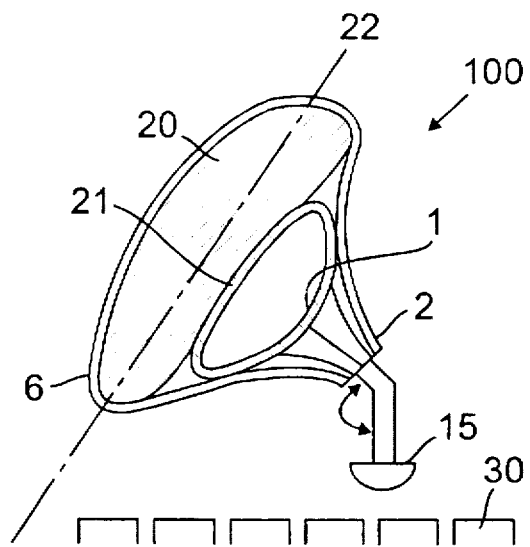
FIG. 3 is a cut-away view of the manipulation aid of FIG. 1 shown mounted to the hand of a user proximate a keyboard.

FIG. 3 is a cut-away view of the manipulation aid 100 of the present invention shown mounted on a user's hand 20 and disposed above keys 30 of a keyboard. The user actuates the keys by moving his hand down toward the keyboard such that the tip 15 engages and displaces a key. The flexible tube 1 is compressed against the palm 21 of the hand by the pressure created by the straps 6. The tube 1 acts as a cushion and a spacer, creating a more comfortable feel for the user while maintaining the cone 2 a distance removed from the palm so that the tip 15 can be more easily seen and controlled by the user.

Plane 22 extends through the hand 20 parallel to the palm. In a relaxed state, the hand may be slightly rotated so that plane 22 is at an angle less than 90° with respect to the surface of the keys 30. The disposition of the arm with respect to the hand can be adjusted by positioning the tube at different points on the palm.

Figure 4:
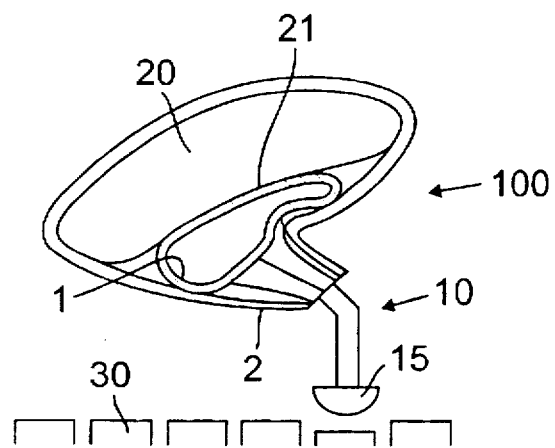
FIG. 4 is a cut-away view of the manipulation aid of FIG. 1 shown in a collapsed state, depressing the keys of a keyboard with excessive force.

FIG. 4 shows a cut away view of the manipulation aid 100 shown in the collapsed state. When excessive force is applied by the user's hand onto the keys 30, the pressure from the keys on the tip 15 will create a torque on the actuator 10 and the cone 2, causing the tube 1 and the cone to collapse. This prevents the user from exerting too much force on the keys or on his hand. Further, if the user rests his hand on a surface, such as a desk, causing the actuator to press onto the surface, the cone and tube will collapse, rather than create an unacceptably high torque on the user's hand. The collapsible cone and tube will also reduce any torque translated to the hand should the actuator catch on anything, such as clothing.

The forgoing description relates to one embodiment of my invention. The invention is defined by the following claims:

I claim:

1. A manipulation aid comprising:
   a cone having a base and an apex;
   an actuator mounted at the apex of the cone; and
   means for attaching the cone to a palm of a user, wherein the cone provides a platform for the actuator, displacing the actuator from the palm of the hand.

2. The manipulation aid of claim 1 wherein the actuator comprises a rod mounted at the apex of the cone and an arm mounted to the rod.

3. The manipulation aid of claim 1 wherein the cone comprises a flexible material.

4. The manipulation aid of claim 3 wherein the cone is hollow.

5. The manipulation aid of claim 1 wherein the attaching means is a strap mounted to the base of the cone.

6. The manipulation aid of claim 5 wherein the cone and the strap are integrally formed.

7. The manipulation aid of claim 6 wherein the cone and strap comprise a flexible material.

8. The manipulation aid of claim 5 further comprising a spacer disposed on the strap near the base such that the spacer is disposed between the palm and the base when the strap is engaged to the palm.

9. The manipulation aid of claim 8 wherein the spacer is a tube.

10. The manipulation aid of claim 5 further comprising a cushion mounted to the strap near the base such that the cushion is disposed between the base and the palm of the user.

11. The manipulation aid of claim 10 wherein the cushion is a tube.

12. The manipulation aid of claim 1 further comprising a spacer disposed at the base of the cone.

13. A manipulation aid, which, in use, is engaged to a body part of a user, the manipulation aid comprising:
   a projection extending away from the body part when in said use;
   a strap mounted to the projection, the strap for securing the projection to the body part; and
   an actuator mounted to the projection distal to the body part such that the actuator is visible to the user, wherein the actuator is substantially inflexible and has a fixed orientation with respect to the projection.

14. The manipulation aid of claim 13 wherein the projection collapses when in use under a predetermined load applied by the user.

15. The manipulation aid of claim 14 wherein the projection is elastic such that it returns to original shape after the predetermined load is removed.

16. The manipulation aid of claim 15 wherein the projection comprises a cone.

17. The manipulation aid of claim 16 further comprising a tip mounted to the actuator distal to the cone.

18. A pointing stick that attaches to a user's hand for use in actuating a device, comprising:
   a platform;
   a means for securing the platform to the hand; and
   an actuator comprising a first part and a second part, wherein an end of the first part of the actuator is mounted to the platform and the first part of the actuator extends perpendicular to a palm of the hand, and the second part of the actuator is disposed at an angle relative to the first part, wherein,
   the angle is selected so that when in use, the second part of the actuator is substantially perpendicular to the device to actuate it.

19. The pointing stick of claim 18 wherein the first part of the actuator comprises a rod and the second part of the actuator is an arm mounted to the rod.

20. The pointing stick of claim 19 wherein the arm is disposed perpendicular to the rod.

21. The pointing stick of claim 18 further comprising a cushion mounted to the securing means near the platform.

22. The pointing stick of claim 21 wherein the cushion comprises a flexible tube.

23. The pointing stick of claim 18 further comprising a spacer mounted to the platform whereby the platform is displaced from the palm.

24. The pointing stick of claim 23 wherein the spacer is flexible.

25. The pointing stick of claim 23 wherein the spacer is a tube.

26. The pointing stick of claim 18 wherein the platform and the securing means are integrally formed.

27. The pointing stick of claim 18 wherein the platform is a collapsible cone.

28. An apparatus for pointing comprising:

means for preventing a user from exerting too much force with the apparatus;

a harness attached to said means, the harness for engaging a human body part; and an actuator mounted to the means distal to the harness.

29. The apparatus of claim 28 wherein the projection is elastic such that it returns to its original shape when the load is removed.

30. The apparatus of claim 29 wherein the projection extends from the body part such that the actuator can be easily seen by the user.

31. The apparatus for pointing of claim 28 wherein the means comprises a projection that collapses under a predetermined load.

32. A manipulator for attachment to the limb of a user comprising:

a flexible tube having an exterior wall;

a collapsible cone having a base and an apex, wherein the base is mounted at the exterior wall of the tube;

a rod mounted to the apex of the cone;

a first strap mounted to the exterior wall of the tube at a first side of the cone;

a second strap mounted to the exterior wall of the tube at a second side of the cone;

a clasp attached at a first end to the first strap and attached at a second end to the second strap.

33. The apparatus of claim 32 further comprising an arm mounted to the rod.

34. A manipulation aid comprising:

a cone having a base and an apex;

an actuator mounted at the apex of the cone;

a strap mounted to the base of the cone for attaching the cone to a limb of a user; and, a spacer disposed on the strap near the base such that the spacer is disposed between the limb and the base when the strap is engaged to the limb.

35. The manipulation aid of claim 34, and farther wherein the spacer is a tube.

* * * * *